United States Patent
Roberts

(10) Patent No.: US 9,008,267 B2
(45) Date of Patent: Apr. 14, 2015

(54) MEDICAL VIEWING SYSTEM FOR DISPLAYING AN X-RAY IMAGE

(75) Inventor: Johannes Hendrik Roberts, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 434 days.

(21) Appl. No.: 13/147,862

(22) PCT Filed: Feb. 8, 2010

(86) PCT No.: PCT/IB2010/050547
§ 371 (c)(1),
(2), (4) Date: Aug. 4, 2011

(87) PCT Pub. No.: WO2010/092516
PCT Pub. Date: Aug. 19, 2010

(65) Prior Publication Data
US 2011/0293069 A1    Dec. 1, 2011

(30) Foreign Application Priority Data

Feb. 10, 2009  (EP) .................................... 09152466

(51) Int. Cl.
G21K 1/04     (2006.01)
G01N 23/04    (2006.01)
H05G 1/64     (2006.01)
A61B 6/06     (2006.01)
A61B 6/00     (2006.01)

(52) U.S. Cl.
CPC ................. *A61B 6/06* (2013.01); *A61B 6/4035* (2013.01); *G21K 1/046* (2013.01); *A61B 6/4441* (2013.01)

(58) Field of Classification Search
CPC ........... G21K 1/00; G21K 1/04; G21K 1/046; G01N 23/04; H05G 1/64; H01J 31/50
USPC ........ 378/20, 62, 91, 98, 98.8, 147–153, 160, 378/204, 210, 901
See application file for complete search history.

(56) References Cited

U.S. PATENT DOCUMENTS

| 2,295,975 | A | * | 9/1942 | Storm ........................... 378/153 |
| 4,093,864 | A | * | 6/1978 | Hahn et al. ..................... 378/152 |
| 4,514,859 | A | * | 4/1985 | Holzermer ..................... 378/152 |
| 4,752,947 | A | * | 6/1988 | Telorack ........................ 378/152 |
| 5,644,614 | A | * | 7/1997 | Toth et al. ...................... 378/147 |

(Continued)

FOREIGN PATENT DOCUMENTS

| EP | 1720173 | 11/2006 |
| JP | 2009011466 | 1/2009 |

*Primary Examiner* — Anastasia Midkiff

(57) ABSTRACT

A medical viewing system comprises an X-ray source, a collimator for limiting the X-ray radiation output of the X-ray source and a flat X-ray detector, wherein the collimator is adjustable such that the subsequent X-ray images acquired by the X-ray detector comprise a rectangular shape with variably rounded corners. The acquired X-ray images have a shape, which is in-between a circular shape and a rectangular or square shape. Acquired images with this shape may then be displayed on a display unit, wherein the borders or the images are distant from the borders of the designated screen area of the display unit in order to define a gap on the display. On rotation of an acquired image the rounded corners move towards the borders of the screen and are dimensioned such that they never cross the borders of the display. The used area of the screen 30 is approximately 30% larger than that of a circular image, e.g. taken by means of an image intensifier.

15 Claims, 3 Drawing Sheets

(56) References Cited

U.S. PATENT DOCUMENTS

| | | |
|---|---|---|
| 6,542,573 B2 | 4/2003 | Schomberg |
| 7,391,848 B2 | 6/2008 | Spahn |
| 7,734,016 B2 | 6/2010 | Watanabe |
| 2004/0264646 A1 | 12/2004 | Spahn |
| 2006/0126797 A1 | 6/2006 | Hoernig |

* cited by examiner

MEDICAL VIEWING SYSTEM FOR DISPLAYING AN X-RAY IMAGE

FIELD OF THE INVENTION

The present invention is related to an X-ray image acquisition device, a medical viewing system and a method for displaying of X-ray images.

BACKGROUND OF THE INVENTION

Images from a flat-panel X-ray detector (FD) are square or rectangular. Images acquired from such an X-ray detector will normally be displayed in the same form on a display unit, e.g. a monitor. If it is necessary to rotate an acquired image, corners of the rectangular image will turn outside of the displayed area and are no longer visible, especially in a zoom mode.

Images acquired from a conventional X-ray image intensifier (II) are circularly shaped and thus are easily to rotate. It is not favourable to use circular images, because a circular image contains much less information than a square or rectangular image with the same overall dimensions.

SUMMARY OF THE INVENTION

It may be possible to acquire square or rectangular images by a flat-panel X-ray detector and display these images shrunk (zoomed out) on a display in order to be able to rotate it without losing information. This is not desirable, because only a small fraction of the display would be used and a lot of space on the display would be wasted. Additionally, for the purpose of rotating an already acquired X-ray image the rotation of the flat-panel X-ray detector is not an option, because this means further exposition of the patient to X-rays.

Accordingly, the use of rectangular or circular X-ray images is not favourable, when the acquired image needs to be rotated regularly, because the display space would not be used optimally.

Accordingly, there may be a need for a medical viewing system which may allow to overcome at least some of the above insufficiencies. Particularly, there may be a need for a medical viewing system that provides for acquiring X-ray images by means of a flat-panel X-ray detector, wherein the acquired images use the space of the display optimally and provide for the ability of rotating them without losing information during the rotation process.

These needs may be reached with an X-ray image acquisition device, a medical viewing system, a method, a computer program element and a computer-readable medium according to the independent claims. Various embodiments of the present invention are described in the dependent claims.

The medical viewing system according to the present invention takes advantage of X-ray images with a shape, which is in-between a circular shape and a rectangular or square shape. This means, that a display unit, which may be comprised in the medical viewing system according to the present invention, may able to show X-ray images that are defined by e.g. a square or a rectangular shape with rounded corners. It is noted that, instead of stating "square or rectangular" only the expression "rectangular" will be used in the following description, since square shapes are also covered by the expression "rectangular".

There are at least two options how to produce X-ray images with such a shape. For example, a square flat-panel X-ray detector may acquire a rectangular image and a calculation unit, which may be comprised in the medical viewing system according to the present invention, crops the acquired image so that its corners are rounded. This method may not be allowed according to health issues since it exposes the patient to more X-ray radiation than necessary for the examination. Hence, it is more preferred to reduce the exposition of the patient to X-rays and to adapt the X-ray source in a way that only X-ray images with a shape described above can be acquired. Therefore, a collimator for limiting the X-ray radiation output of the X-ray source may be comprised in the X-ray image acquisition device in order to adapt the X-ray source for the X-ray exposition area comprises the shape as described above.

Acquired images with this shape may then be displayed on the display unit, wherein the borders or the images are distant from the borders of the designated screen area of the display unit in order to define a gap on the display. On rotation of the image the rounded corners move towards the borders of the screen and are preferably dimensioned such that they never cross the borders of the display. At a rotation of e.g. 45° of a rectangular image with rounded corners the rounded corners may just touch the borders of the display.

Therefore, by shaping the acquired images in the described way, the images can be rotated on a display without the loss of information during rotation. Additionally, in the case of square images with rounded corners the image area is approximately 30% larger than of the image area of a circular image with a maximum possible diameter for the related display. The display may therefore be optimally used considering the needed degree of rotation of the acquired images.

In an exemplary embodiment of the present invention in the medical viewing system a collimator may be comprised to limit the X-ray exposition onto the patient to be examined. This collimator is preferably adapted to change its shape from a rectangular shape to a rectangular square shape with rounded corners. The collimator can comprise any means that allow to round the edges of a rectangular opening or the such, e.g. corner elements with a concave or arc-shaped edge that may be advanced into the corners of the rectangular original shape of the collimator to cover the corners. This also leads to the ability of extending an X-ray radiation output area from the X-ray source from a rectangular shape with rounded corners to a fully rectangular shape when rotation of the image should not be needed during the examination procedure. Vice versa, when rotation is needed, the exemplary corner elements may be advanced into the corners of the rectangular shape of the collimator in order to optimally adjust the described shape of acquired images.

In an exemplary embodiment of the present invention, the image is zoomed to fit the designated screen area on the display unit when rotation is not needed and the corner elements of the collimator are outside the rectangular area. By this feature, the maximum display area can be used, e.g. for cardiovascular interventions, where rotation may not be necessary.

If only a small degree of rotation is needed, the corner rounding may be gradually inserted, so that the maximum amount of image information is available. If the examination is used for acquiring live images, e.g. during interventions, the rounding may be accomplished in real-time, if the live images need to be rotated.

Preferably, the medical viewing system comprises a calculation unit, which may be adapted to control the adjusting process of the collimator shape depending on the needed degree of rotation during the present examination. This reduces the workload on the user of the medical viewing system who would otherwise need to insert or remove the corner elements or the such into the corners of the collimator.

In a further preferred embodiment of the present invention, the calculation unit may be adapted for automatically zooming out the acquired image, when a rotation is needed in order to distance the image borders from the display borders. Additionally, this zooming feature can be coupled to the adjusting process of the collimator shape.

Further exemplary embodiments of the medical viewing system and the X-ray image acquisition device, which may be comprised within the medical viewing system according to the present invention are set forth in the dependent claims. The expected advantages discussed in relation to the exemplary embodiments of the medical viewing system and the X-ray image acquisition device described above also apply to the described exemplary embodiments of the method according to the present invention and vice versa.

According to another exemplary embodiment of the present invention, a computer-readable medium is provided in which a computer program for adapting the collimator, zooming the acquired images and rotating the acquired images is stored which, when being executed by a processor, causes the processor to carry out the above-mentioned steps.

Furthermore, according to another exemplary embodiment of the present invention, a computer program element for controlling the adjusting process of the collimator shape and the rotation and zooming of the medical images on the display unit is provided which, when being executed by a processor, causes the processor to carry out the above-mentioned steps.

Those skilled in the art will readily appreciate that the method of adjusting the collimator to the desired image shapes, the zooming and rotating of the acquired images according to the invention may be embodied as a computer program, i.e. by software or may be embodied using one or more special electronic optimization circuits, i.e. in hardware, or the method may be embodied in hybrid form, i.e. by means of software components and hardware components.

This exemplary embodiment of the invention covers both a computer program that uses the invention right from the beginning and a computer program that turns an existing program into a program that uses the invention by means of update. Further on, the computer program element may be able to provide all necessary steps to fulfil the procedure of the method as described above.

According to a further exemplary embodiment of the present invention, a medium for making a computer program element available for downloading is provided, which computer program element is arranged to perform the method, according to one of the previously described embodiments of the invention.

For example, existing medical viewing systems may be upgraded with a new software, which, when being executed on a processor, causes the system to carry out the above-mentioned steps in zooming and rotating of acquired images and adapting the shape of a collimator according to the invention.

It has to be noted that features and side effects of the present invention have been described with reference to different embodiments of the invention. However, a person skilled in the art will gather from the above and the following description that unless other notified, in addition to any combination or features belonging to one embodiment also any combinations between features relating to different embodiments or to a manufacturing method is considered to be disclosed with this application.

BRIEF DESCRIPTION OF THE DRAWINGS

Features and desired effects of the present invention will be further described with respect to specific embodiments as shown in the accompanying figures but to which the invention shall not be limited. The drawings in the figures are only schematically and not to scale. Similar elements in the figures are referred to with similar reference signs.

DETAILED DESCRIPTION OF EMBODIMENTS

Figure 1A:
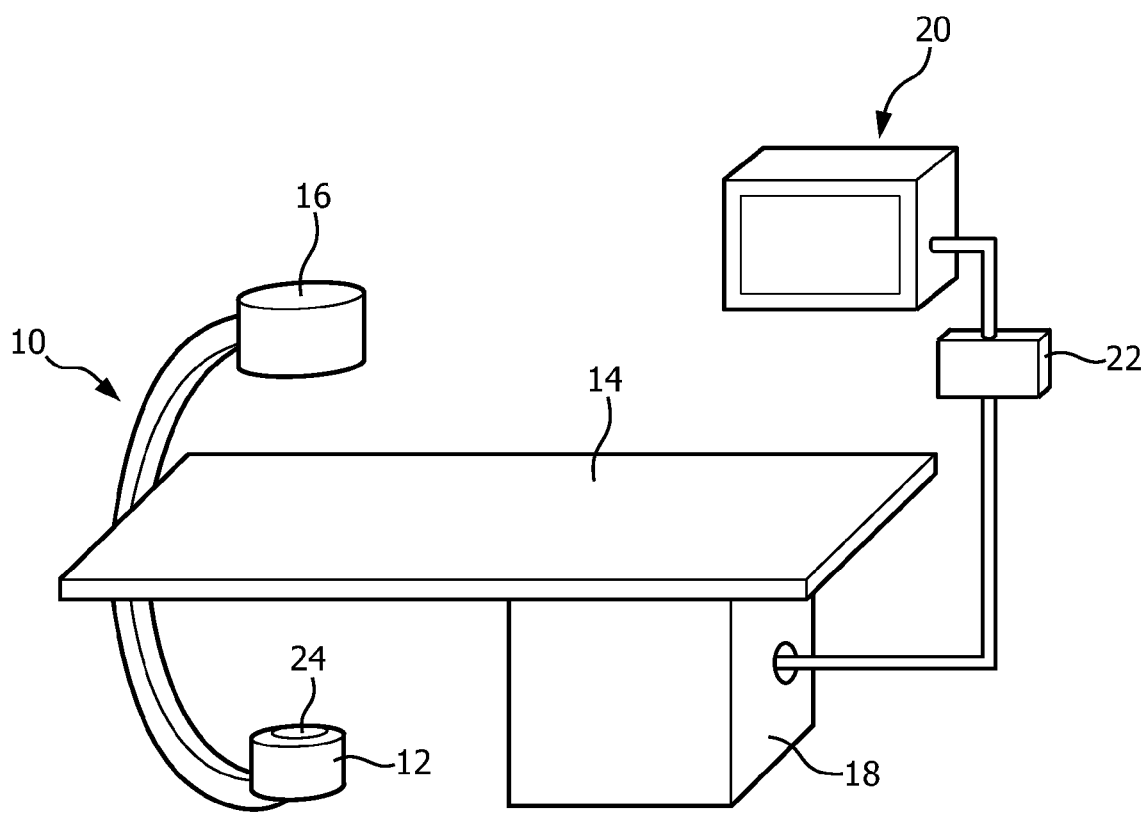
FIG. 1a shows a medical viewing system according to the invention.

FIG. 1a schematically shows a medical viewing system 10 comprising an X-ray image acquisition device with a source of X-ray radiation 12 provided to generate X-ray radiation. A table 14 is provided to receive a subject to be examined. Further a flat X-ray image detector 16 is located opposite to the source of X-ray radiation 12. During the radiation procedure the examined subject is located between the source of X-ray radiation 12 and the detection module 16. The latter sends data to a data processing unit or calculation unit 18, which is connected to both the X-ray image detector 16 and the X-ray radiation source 12.

The calculation unit 18 is exemplarily located underneath the table 14 for saving space within the examination room. Of course, it could also be located at a different place, such as in a different room or a different laboratory.

Furthermore, a display unit 20 is arranged in the vicinity of the table 14 for displaying information to the person operating the medical viewing system, which can be a clinician such as a cardiologist or cardiac surgeon. Preferably, the display unit 20 is movably mounted to allow for individual adjustment depending on the examination situation. Also, an interface unit 22 is arranged to input information by the user.

Basically, the image detector 16 generates images by exposing the subject to X-ray radiation, wherein said images are further processed in the calculation unit 18. It is noted, that the example shown is of a so-called C-type X-ray image acquisition device. The X-ray image acquisition device comprises an arm in form of a C where the image detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

In order to limit the exposition of the subject to be examined to X-rays, the source of X-rays 12 comprises a collimator 24 that may have non-transparent closure parts and semi-transparent diaphragm wedges whose adjustment makes is possible to shape the X-ray radiation output (the X-ray radiation beam) in such a way that only parts of the patient's body that are of interest are irradiated with the desired radiation intensity.

Figure 1B:
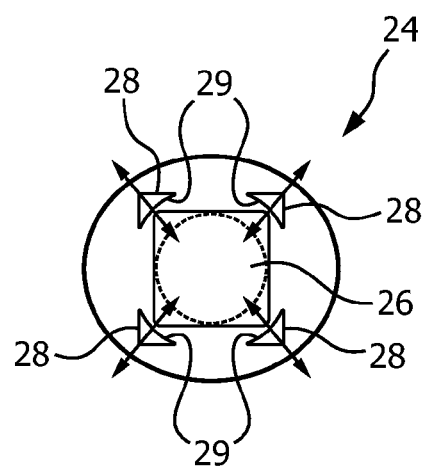
FIG. 1b shows a top-view of a collimator of the X-ray image acquisition device according to the invention.

In FIG. 1b a top view of the collimator 24 is shown, where a basic rectangular X-ray radiation output area 26 is shown. On the corners of this area 26 four corner elements 28 are shown comprising at least one arc-formed edge 29 for variably rounding the corners of a rectangular X-ray radiation output area that are movably supported in the collimator 24 for variably covering the corners of the area 26. If the corner elements 28 are fully swept back or moved outside the area 26 a rectangular X-ray radiation beam appears on the X-ray detector 16. On gradually inserting the corner elements 18 into the area 26 the rounding of the corners gradually increases.

Figure 2:
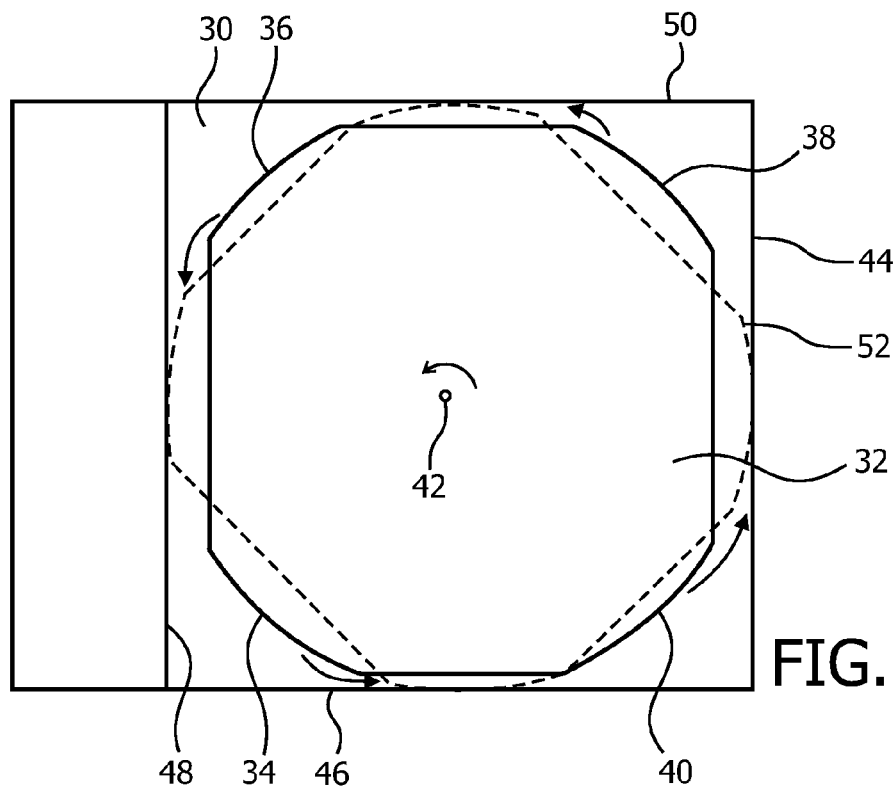
FIG. 2 schematically shows a screen area with an acquired image shaped according to the present invention.

In FIG. 2 a screen 30 of the display unit 20 is shown, wherein an acquired X-ray image 32 is shown. Exemplarily, the acquired image 32 is derived from a rectangular shape with additionally rounded corners 34-40. These corners are shaped such that the image 28 can be rotated inside the screen 30 around its centre 42 whereby the corners 34-40 do not cross the borders 40-46 of the display area 30.

Shown with dashed lines 52 is an image which is the acquired image 32 rotated by 45° counter-clockwise. It can thereby be seen, that the screen area 30 is optimally used by the acquired image 32. The used area of the screen 30 is approximately 30% larger than that of a circular image, e.g. taken by means of an image intensifier, with a diameter that extends e.g. from border 44 to 48.

Figure 3:
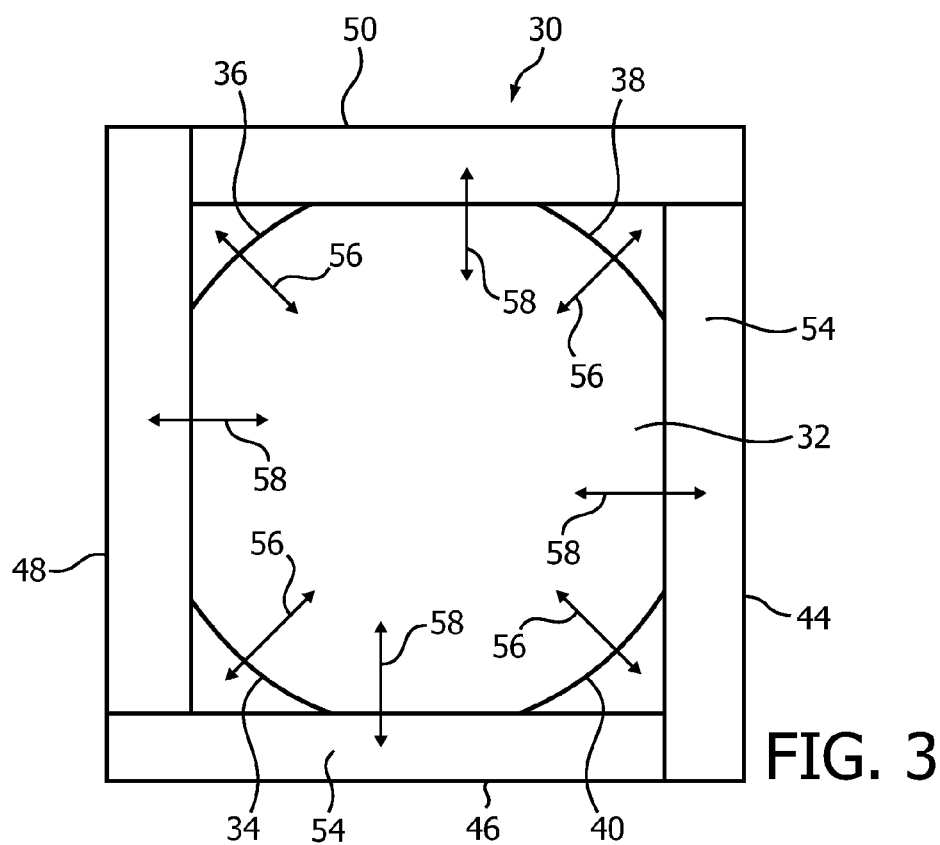
FIG. 3 schematically shows a screen area with an acquired image adapted to the purpose or present examination.

In FIG. 3 an acquired image 32 is shown displayed on a display area 30. Between the borders 44-50 and the acquired image 32 is a gap 54 that allows for rotation of the acquired image 32. If rotation is not necessary, the corners 34-40 do not need to be rounded. Therefore, the corners 34-40 are restored to conventional rectangular corners, as indicated by the arrows 56.

The rounded corners correspond to the adjustment of the collimator 24, e.g. by advancing or retracting corner elements 28 into the X-ray radiation beam.

In case the corners 34-40 are rectangular and rotation is not needed, the acquired image 32 may then be zoomed to fit the display area 30 completely, as indicated by the arrows 58.

Preferably, the calculation unit 18 is adapted to control the collimator 24 and the display unit 20 in order to adapt the corner rounding and the zoom factor of the acquired image 32 according to the given need of rotational degree that may depend on the kind of examination.

Figure 4:
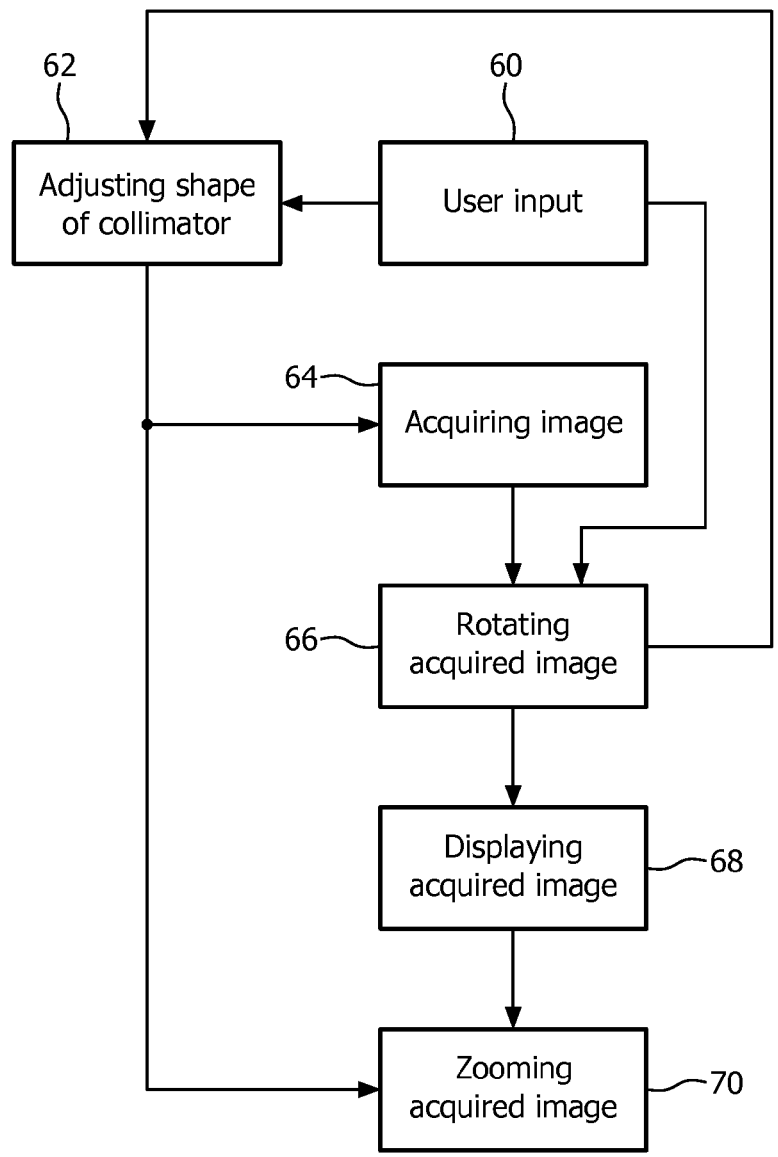
FIG. 4 schematically shows the method steps according to the present invention.

In FIG. 4 the method according to the present invention is described schematically. Depending on various user inputs 60 the collimator 24 is adjusted to change its shape 62 according to the related purpose and the need of rotational degree. Thereafter, the X-ray images 32 are acquired 64.

After that, on user inputs 60, which may be introduced at the user interface 22 and lead to sending a signal to the display unit 20 or the calculation unit 18, the acquired image 32 may be rotated 66.

If necessary, e.g. if the present shape of the acquired image 32 does not allow rotation on the screen 30, the collimator 24 may be caused to round the corners of the X-ray radiation output area in order to adjust the shape of the acquired image 32. If rotation is not required anymore, the corners are restored to a rectangular shape. Therefore, a feedback to the adjusting process of the collimator 24 is preferable.

After acquiring the images 32 they are displayed 68 on the display unit 20. Depending on the need for rotation the images may also be zoomed in or zoomed out 70.

While the invention has been illustrated and described in detail in the drawings and foregoing description, such illustration and description are to be considered illustrative or exemplary and not restrictive; the invention is not limited to the disclosed embodiments.

List of Reference Signs
   10 medical viewing system
   12 X-ray radiation source
   14 table
   16 flat X-ray detector
   18 calculation unit
   20 display unit
   22 user interface
   24 collimator
   26 X-ray radiation output area
   28 corner elements
   29 arc-formed edge of collimator element
   30 display area
   32 acquired image
   34 corner
   36 corner
   38 corner
   40 corner
   42 center of acquired image
   44 border of display area
   46 border of display area
   48 border of display area
   50 border of display area
   52 rotated acquired image
   54 gap
   56 rounding of corners
   58 zooming of acquired image
   60 user input
   62 adjusting shape of collimator
   64 acquiring image
   66 displaying acquired image
   68 rotating acquired image
   70 zooming acquired image

The invention claimed is:

1. A medical viewing system, comprising:
an X-ray image acquisition device comprising a flat X-ray detector and an X-ray source, said source comprising a collimator;
a display unit; and
a calculation unit connected to said X-ray image acquisition device and said display unit,
said collimator being adjustable such as to cause an X-ray image acquired by the X-ray detector from X-ray radiation collimated by said collimator to have a rectangular shape with rounded corners, the rounding being variable in accordance with the adjustment,
wherein the calculation unit is configured for displaying the acquired image on the display unit, and by said displaying enclosing a variable gap between the borders of the image and the borders of the display unit such that the image is rotatable without intersecting the borders of the display unit.

2. The system according to claim 1, wherein the collimator comprises movably supported corner elements comprising at least one arc-formed edge for variably rounding the corners of a rectangular X-ray radiation output area.

3. The system according to claim 1, wherein the collimator is connected with the calculation unit for adjusting, according to a signal of the calculation unit, the rounding of said shape.

4. The system according to claim 1, wherein the calculation unit is configured for determining the gap and the roundness of the corners needed for rotation of the image according to a given needed degree of rotation.

5. The system according to claim 1, wherein the calculation unit is configured for determining a degree of rotation needed to accomplish a given examination.

6. The system according to claim 1, wherein the calculation unit is configured for adjusting a shape of said collimator gradually in real time.

7. A method for displaying X-ray images, comprising the steps:
adjusting a collimator such that the subsequent X-ray images acquired by an X-ray detector comprise a rectangular shape with variably rounded corners;

acquiring an X-ray image by means of an X-ray image acquisition device;

zooming the acquired image; and displaying the zoomed acquired image.

8. The method according to claim 7, further comprising rotating the acquired image.

9. A non-transitory computer readable medium embodying a program having instructions executable by a processor to perform a plurality of acts, among said plurality there being the acts of:

adjusting a collimator such that an X-ray image acquired via an X-ray detector after collimation by the collimator comprises a rectangular shape with variably rounded corners;

acquiring said X-ray image;

adjusting, according to a signal of a calculation unit, an amount of rounding of said shape; and displaying the acquired image having the adjusted shape.

10. The computer readable medium of claim 9, among said plurality there being the act of rotating the acquired image.

11. The computer readable medium of claim 9, among said plurality there being the act of zooming the acquired image.

12. The computer readable medium of claim 9, the collimator comprising movably supported corner elements comprising at least one arc-formed edge, among said plurality there being the act of using said edge for variably rounding the corners of a rectangular X-ray radiation output area.

13. The computer readable medium of claim 9, among said plurality there being the acts of:

acquiring multiple X-ray images via respective X-ray beams collimated by collimation, said image being among the acquired images; and displaying said multiple images on the display unit, and by said displaying enclosing a variable gap between the borders of the image and the borders of the display unit such that the image is rotatable without intersecting the borders of the display unit.

14. The computer readable medium of claim 9, the amount of the rounding depending upon a given maximum degree of rotation, of the acquired image, for said displaying.

15. The computer readable medium of claim 9, the amount of the rounding depending upon a degree of rotation needed to accomplish a given examination.

* * * * *